United States Patent [19]

Ball et al.

[11] Patent Number: 4,896,324

[45] Date of Patent: Jan. 23, 1990

[54] METHOD AND APPARATUS FOR OPTIMIZING COUPLED LASER RESONATOR PERFORMANCE

[75] Inventors: Gary A. Ball, Newington; Michael C. Fowler, Farmington, both of Conn.

[73] Assignee: United Technologies Corporation, Hartford, Conn.

[21] Appl. No.: 288,301

[22] Filed: Dec. 22, 1988

[51] Int. Cl.⁴ .............................................. H01S 3/098
[52] U.S. Cl. ........................................ 372/18; 372/32; 372/20
[58] Field of Search ...................... 372/20, 18, 28, 25, 372/26, 29, 32

[56] References Cited

U.S. PATENT DOCUMENTS

| | | | |
|---|---|---|---|
| 3,437,955 | 4/1969 | Enloe et al. | 372/29 |
| 4,434,490 | 2/1984 | Kavaya et al. | 372/32 |
| 4,666,295 | 5/1987 | Duvall, III et al. | 372/32 |
| 4,685,111 | 8/1987 | Baer | 372/29 |

Primary Examiner—Léon Scott, Jr.
Attorney, Agent, or Firm—McCormick, Paulding & Huber

[57] ABSTRACT

A method and apparatus for frequency coupling laser resonators and optimizing the performance thereof includes a displaceable mirror for varying the cavity length of a resonator and a controller for selecting the cavity length. The apparatus includes a spectrophone which provides a feedback signal which is dependent only upon the resonator beam frequency.

3 Claims, 2 Drawing Sheets

4,896,324

METHOD AND APPARATUS FOR OPTIMIZING COUPLED LASER RESONATOR PERFORMANCE

TECHNICAL FIELD

This invention relates to coupled laser resonators and more particularly to a method and apparatus which adjusts the cavity length of laser resonator to selectively control laser resonator frequency.

BACKGROUND OF THE INVENTION

Known techniques used to select and maintain laser resonator frequency of coupled resonators require that a portion of the output beam from each resonator be combined and interfered. The resulting interference pattern is a function of three parameters, the frequency of the beams as well as the relative phase and coherence therebetween. As is well known, differences in coherence and phase between the two beams will alter the interference pattern, as will differences in frequency. The techniques which rely on beam interference to maintain optically coupled resonators must account for the effects of these other parameters. The intensity of the beams as well as such parameters as the coupling path length must be determined. Consequently, these known techniques are characterized by undesirably elaborate apparatus and additional measurements.

It would be advantageous to have a method and apparatus for maintaining laser resonators at a selected frequency which would not be effected by variations in beam phase and coherence. The present invention is drawn toward such a method and apparatus.

SUMMARY OF THE INVENTION

An object of the present invention is to provide a method and apparatus for selecting the frequency of a laser resonator.

Another object of the present invention is to provide for a method and apparatus for actively controlling the cavity lengths of coupler laser resonators to maintain frequency locking of the resonator beams that is independent of the phase and coherence thereof.

Another object of the invention is to provide an apparatus for actively controlling the cavity lengths of coupled laser resonators that directly peaks the power of the resonator beams.

According to the present invention, an apparatus for adjusting the electromagnetic frequency $\nu$ of a beam output from an electromagnetic resonator having a gain medium with a maximum value thereof to be equal to a selected electromagnetic frequency, $\nu_r$ includes a displaceable mirror that receives control signals and is configured with the resonator. The displaceable mirror is for selecting the cavity length of the resonator. A mechanism is included for sampling the beam and generating signals indicative of the electromagnetic frequency thereof independent of the coherence or phase thereof. A controller is included that receives the sampled mechanism signals and generates therefrom mirror control signals to position the mirror such that the electromagnetic frequency equals the selected frequency.

According to another aspect of the present invention an apparatus for actively controlling the cavity length of coupled first and second laser resonators whose output beams are locked at a frequency $\nu_0$ with each resonator having a gain medium having a maximum value thereof corresponding to the frequency $\nu_0$ includes a plurality of displaceable mirrors that receive control signals. Each mirror is configured with a respective one of the resonators and selects the cavity length thereof. A mechanism is included for sampling each beam and generating therefrom signals indicative of the electromagnetic frequency thereof independent of a coherence and phase thereof. A controller is included for receiving the sampled signals and generating mirror control signals to position the mirrors such that the cavity lengths of the respective resonators are equal thereby ensuring that the frequencies of the laser resonator output beams remains locked at $\nu_0$.

DESCRIPTION OF THE PREFERRED EMBODIMENT

Figure 1:
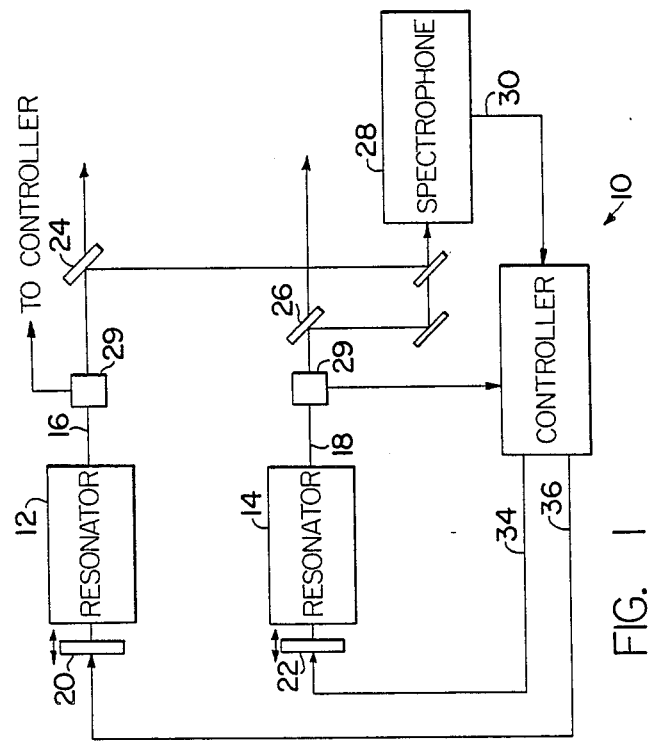
FIG. 1 is a simplified schematic illustration including an apparatus provided according to the present invention.

FIG. 1 is a diagrammatic illustration including an apparatus provided according to the present invention capable of adjusting the cavity lengths of a laser resonator so that the frequency of the output beam is equal to a selected value. The apparatus 10 includes first and second resonators 12 and 14, each having an output beam 16 and 18. The laser resonators are of a type known in the art and can comprise a carbon dioxide ($CO_2$) laser lasing at the 10.6 micron wavelength line.

The apparatus also preferably includes a displaceable mirror 20 and 22 for each of the laser resonators which receives the beams 16 and 18, respectively. The mirrors are conventional and, as detailed hereinafter, can be dithered or displaced in order to vary the resonator cavity path length and hence, the resonator output beam frequency.

Beam splitters 24 and 26 sample the output beams and provide the sampled beams to spectrophone 28. The spectrophone contains a gaseous medium whose optical absorption as a function of frequency has a maximum absorption that can be configured to coincide with a selected frequency of the resonator output beam. As detailed hereinafter, it is not preferable to select the spectrophone's medium absorption line maximum to coincide with the maximum of the main curve of the resonator. Alternatively, the spectrophone can be filled with a gas whose maximum absorption is displaced from the desired frequency of the laser resonator's output beam such that the normalized spectrophone output signal, S, varies monotonically in magnitude with frequency about the desired frequency.

Typically, a beam output from a laser resonator is optically modulated (chopped) at its own carrier frequency before being presented to the spectrophone. The spectrophone converts energy from the chopped laser beam to an acoustic signal at the laser beam's carrier frequency. Readily measurable acoustic signals are obtained even when the fractional absorption of optical beam power is small. The amplitude of the signal output from the spectrophone is proportional to the optical absorption of the spectrophone medium. Although the spectrophone of FIG. 1 is configured to receive sampled beams, those skilled in the art will note that spectrophones absorb little power and the apparatus 10 could alternatively be configured to fully receive both beams 16 and 18. The apparatus 10 also comprises a device 29 which measures the output power of the beams.

The spectrophone provides an output signal on line 30 to controller 32. The controller is of a known type and comprises such computation and memory means as is necessary to perform the functions detailed herein. As detailed hereinafter, the controller generates control signals on lines 34 and 36 to position the mirrors at the desired cavity length. The controller incorporates an algorithm which utilizes the signal from the spectrophone as a feedback signal.

Figure 2:
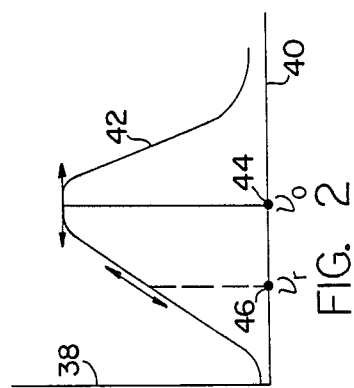
FIG. 2 is a diagrammatic illustration of a first characteristic of the apparatus of FIG. 1.

FIG. 2 is a diagrammatic illustration showing the frequency dependence of the absorption medium in the spectrophone of FIG. 1. Axis 38 corresponds to absorption while axis 40 corresponds to frequency. Curve 42 corresponds to the collision broadened optical absorption line of the absorption medium in the spectrophone. The frequency at which the spectrophone medium has a maximum absorption corresponds to $\nu_0$ (point 44) while point 46 is the desired frequency, $\nu_r$, of the output beam of a resonator, such as resonator 12.

For a collision broadened absorption line such as is characteristic of the medium of the spectrophone, the frequency dependence of the absorption medium, and therefore, the spectrophone output is given by $$k(\nu) = k(\nu_0)/1 + ((\nu - \nu_0)/\gamma^2)$$

where $\nu_0$ is the absorption line center frequency and $\nu$ is the absorption line half width at half height. The fractional change in spectrophone signal per longitudinal cavity mode is given by $(2L)^{-1}$ where L is the cavity length and $\gamma$, expressed in inverse centimeters, is on the order of 0.05 to 0.1 cm$^{-1}$ for infrared transitions.

After a laser resonator has been made operational and has been generally configured using known techniques, the cavity length and hence the optical frequency of one or more similar uncoupled laser resonators can be precisely adjusted to a preselected value with the spectrophone configured in the manner described hereinabove with respect to FIG. 2. The signal output from the spectrophone, $S(\nu)$ at each frequency in a selected band of laser resonator carrier frequencies is normalized by the controller to the corresponding resonator output power, $P(\nu)$. The normalized spectrophone signal varies monotonically in magnitude with absorption. As shown in FIG. 2, the selected first resonator frequency $\nu_r$ displaced from the spectrophone medium absorption center line frequency $\nu_0$ on the order of one half line width.

The controller then generates signals to displace the first resonator mirror and adjust its cavity length so that the output beam of the resonator is at frequency $\nu_r$. A plurality of similar laser resonators can each be configured to have the same cavity length. The laser resonators can then be optically coupled if desired. As noted above, a distinct advantage of the present invention is that the signal output from the spectrophone is independent of the coherence or phase of a beam and varies only with frequency. Variations in the power normalized signal magnitude presented from the spectrophone correspond directly to variations in laser resonator frequency.

Alternatively, the controller may comprises an algorithm which dithers the mirror position about the selected frequency $\nu_r$, and generates, from the magnitude and phase of the normalized spectrophone output signal, signals to position the mirror with a cavity length corresponding to a resonator beam frequency $\nu_r$. Moreover, those skilled in the art will note that the spectrophone medium can be selected so that the desired resonator frequency $\nu_r$ coincides with other portions of the medium's absorption curve, such as at a maximum, $\nu_0$. In such cases the controller can comprise an appropriate algorithm of a known type (e.g. a "hill climbing" algorithm) to adjust the resonator cavity length to the desired value. For an embodiment where the desired absorption curve and resonator medium gain curve maximum frequencies coincide, it is preferred to select a spectrophone absorption medium whose bandwidth is sufficiently narrow so that a signal maximum is readily discernable by the controller.

The present invention may also be practiced to actively control the cavity length of coupled resonators. As is known, coupled laser resonators will frequency lock if the frequencies of the respective resonator beams are sufficiently close. Without active control of each resonator's optical path length however, frequency locking is inherently unstable since the cavity lengths of the resonators will drift in time. Eventually the resonator cavity length difference will become too great, and the beams will unlock. To frequency lock laser resonators with the present invention, each should have the same gain medium with a maximum power at the frequency $\nu_r$, and each should have the same cavity length within a range L.

Figure 4:
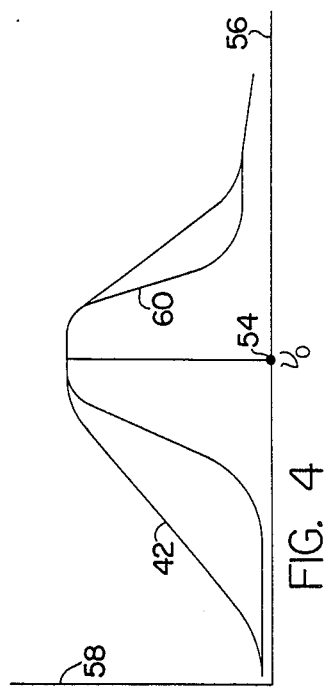
FIG. 4 is a diagrammatic illustration of a characteristic of the apparatus of FIG. 3.
Figure 3:
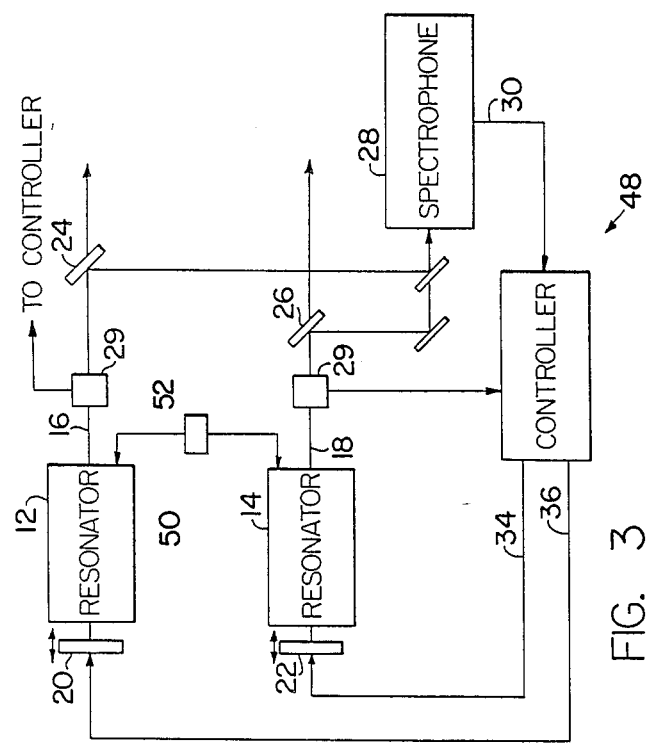
FIG. 3 is a simplified schematic illustration including an alternative apparatus to that of FIG. 1.

An apparatus 48 for providing active cavity length control is schematically shown in FIG. 3. The apparatus 48 is similar to that of FIG. 1 but additionally comprises a mechanism 50 for coupling the beams, including such conventional optical components as are necessary and a device 52 for selectively blocking the beams. The spectrophone medium is selected so that the desired resonator frequency, $\nu_r$, coincides at a maximum, $\nu_0$, of the medium's absorption curve, i.e. $\nu_r = \nu_0$. With the laser resonators uncoupled, the resonator frequencies ($\nu_r$) are adjusted to coincide with the center line frequency $\nu_r$ as detailed above. The resonators are then optically coupled by removing the blocking device. The controller further comprises a "hill-climbing" type servo algorithm which dithers mirror position and hence the cavity length of the resonators about the frequency $\nu_0$ (point 54 in FIG. 4). In FIG. 4, axis 56 corresponds to frequency while axis 58 corresponds to both spectrophone medium absorption and resonator medium gain, respectively. As a result, the spectrophone output signal varies in accordance with resonator frequency. If the cavity length of one or other resonators differs from its selected value, the controller is configured so that the dithering will result in a spectrophone output signal having an amplitude proportional to the difference between the optimum and the present measured value. This signal is again provided to the controller which adjusts mirror position to establish the desired cavity length.

Another advantage of the present invention over the known art lies in that the present invention can be easily configured to maximize the performance of coupled laser resonators. As noted above, coupled resonator performance is optimized when the resonators are equal in optical path length. The resonators, when coupled, do not necessarily have the same optical path length but frequency pull to a dominant supermode whose frequency may not be at the maximum of the resonator medium gain curve. The resonators' output power, therefore, will not be a maximum value unless the resonators cavity lengths are equal. As noted above, the controller dithers the laser resonator frequency about a value that corresponds to the resonator medium gain curve maximum (curve 60 in FIG. 4). Since the absorbing medium in the spectrophone is not saturated, and since the spectrophone is sensitive only to optical frequency, changes in frequency correspond directly to changes in absorption. Therefore, peak measured absorption corresponds to maximum output power for the coupled laser resonators.

Although a spectrophone is preferable, those skilled in the art will note that other apparatus which are frequency sensitive only, such a florescence detector, may be substituted. Spectrophonic detection is preferred over florescence detection since spectrophonic detection is most effective at atmospheric pressure, with no need for a vacuum, further simplifying the apparatus.

Similarly, although the invention has been shown and described with respect to a preferred embodiment thereof, it should be understood by those skilled in the art that various other changes, omissions and additions thereto may be made without departing from the spirit and scope of the present invention.

We claim:

1. An apparatus for use with first and second laser resonators each having a gain medium in a cavity and a displaceable mirror for selecting a resonator cavity length, said resonators providing output beams at an electromagnetic frequency having a beam power with a relative value of phase and coherence, said apparatus comprising;
   a means for adjusting the cavity length of said resonators so that the electromagnetic frequency of said resonator beams are equal to a vaue $v-v0$;
   a means for sampling each resonator beam with a means for providing signals indicative of the power of said resonator beams;
   a means for electromagnetically coupling said beams, thereby ensuring that the frequencies of the laser resonator output beams are locked at a frequency $v=v0$;
   a spectrophone means for sampling each beam for providing signals indicative of the electromagnetic frequency of said beams independent of the coherence and phase thereof, said spectrophone means having an operating range of frequencies with a maximum spectrophone means signal amplitude at an electromagnetic frequency $v0$;
   a controller for receiving said resonator beam power signals and said spectrophone means signals and, for each resonator, said controller for
   normalizing said spectrophone means signals with respect to said resonator beam power signals, thereby ensuring said spectrophone means signals are a function of only said resonator beam frequency;
   generating, for each resonator, from said spectrophone means signals mirror control signals for positioning said mirror at a cavity length such that said spectrophone means signal value is equal to the value thereof at said frequency $v=v0$.

2. A method for use with first and second laser resonators each having a gain medium in a cavity and a displaceable mirror for selecting a resonator cavity length, said resonators generating beams at an electromagnetic frequency having a beam power with a relative value of phase and coherence, said method comprising the steps of:
   adjusting the cavity length of said resonators so that the electromagnetic frequency of said resonator beams are equal to a value $v=v0$;
   sampling each resonator beam with a means for providing signals indicative of the power of said resonator beams;
   electromagnetically coupling said beams, thereby ensuring that the frequencies of the laser resonator output beams are locked at a frequency $v=v0$;
   sampling each resonator beam with a spectrophone means for providing signals indicative of the electromagnetic frequency of said resonator beams independent of the coherence and phase thereof, said spectrophone means having an operating range of frequencies with a maximum spectrophone means signal value at said electromagnetic frequency $v=v0$;
   receiving said resonator beam power signals and said resonator beam frequency signals at a controller and,
   normalizing said spectrophone means signals with respect to said resonator beam power signals, thereby ensuring said spectrophone means signals are a function of only said resonator beam frequency;
   generating, for each resonator, from said spectrophone means signals, mirror control signals for positioning said mirror at a cavity length such that said spectrophone means signal value is equal to the value thereof at said frequency $v=v0$.

3. The method of claim 2 wherein said spectrophone means comprises a florescence detector.

* * * * *